ns Patent [19]

Spence et al.

[11] 4,265,880
[45] May 5, 1981

[54] MICROBIAL INSECTICIDE

[75] Inventors: Kemet D. Spence, Potlatch, Id.; Robert E. Andrews, Pullman, Wash.

[73] Assignee: Battelle Development Corporation, Columbus, Ohio

[21] Appl. No.: 134,325

[22] Filed: Mar. 26, 1980

Related U.S. Application Data

[60] Division of Ser. No. 33,895, Apr. 27, 1979, Pat. No. 4,223,007, and a continuation-in-part of Ser. No. 835,817, Sep. 22, 1977, abandoned.

[51] Int. Cl.³ .................. A01N 15/00; C09D 5/32; C12K 1/08
[52] U.S. Cl. .................................................. 424/93
[58] Field of Search ........................................ 424/93

[56] References Cited

U.S. PATENT DOCUMENTS

| | | | |
|---|---|---|---|
| 3,337,395 | 8/1967 | Page | 424/93 |
| 3,541,203 | 11/1970 | Fogle et al. | 424/93 |
| 3,791,983 | 2/1974 | Maierson et al. | 424/93 |
| 4,056,610 | 11/1977 | Barber et al. | 424/93 |
| 4,223,007 | 9/1980 | Spence et al. | 424/93 |

OTHER PUBLICATIONS

Evreinova T. N. et al. J. Colloid & Interface Sci., 36(1):18–23, May 1971, The Interaction of Biological Macro Molecules in Coacervate Systems.
Kreig, A. J. Invert. Pathol. 25:267–268 (1975), Photo Protection Against Inactivation of Bacillus Thuringionis Spores by Ultraviolet Rays.
WO 79/00155 5 Apr. 1979, PCT/US/78/00080, 12 Sep. 1978, Andrews Re. Spence KD. Microbial Insecticides Battelle Development Corp.

Primary Examiner—Shep K. Rose
Attorney, Agent, or Firm—Finnegan, Henderson, Farabow, Garrett & Dunner

[57] ABSTRACT

An improved microbial insecticide composition, and methods for the production and utilization thereof, are disclosed. The disclosed composition comprises a microbial insect pathogen of viral, bacterial, or fungal origin which is susceptible to sunlight-induced inactivation embedded in a coacervate microbead which is comprised of a nucleic acid, typically RNA, and a proteinaceous material, whereby the microbead structure itself effectively shields the agent from sunlight-induced inactivation. The microbead is typically stabilized by chemical crosslinking.

15 Claims, 12 Drawing Figures

MICROBIAL INSECTICIDE

CROSS-REFERENCE TO RELATED APPLICATION

The present application is a continuation-in-part of U.S. application Ser. No. 835,817, filed Sept. 22, 1977 now abandoned. This is a division of application Ser. No. 33,895 filed Apr. 27, 1979, now U.S. Pat. No. 4,223,007.

BACKGROUND OF THE INVENTION

This invention relates to microbial insecticides. More particularly, the invention relates to a novel microbial insecticide composition and to the production and utilization thereof.

Microbial insecticides of viral, bacterial, or fungal origin offer significant advantages over conventional chemical insecticides. Microbial insect pathogens are generally nontoxic and harmless to other forms of life. In addition, microbial insecticides demonstrate a relatively high degree of specificity, and hence do not endanger beneficial insects. Moreover, a susceptible insect host is quite slow to develop resistance to microbial pathogens. Microbial insecticides may be used in relatively low dosages, may be effectively applied as dusts or sprays, and may be used in combination with chemical insecticides.

For example, the Douglas fir tussock moth nuclear polyhedrosis virus (NPV) is a microbial insect pathogen useful for controlling the tussock moth. Likewise, *Bacillus thuringiensis* (*B.t.*), a spore-forming bacterium, is well-known as a microbial insect pathogen useful against numerous leaf-chewing insects in their larval stages, including, for example, alfalfa caterpillars, tomato hornworms, tobacco hornworms, cabbage loopers, cabbage web worms, army worms, gypsy moths, walnut caterpillars, diamondback moths, cosmopolitan green bettles, European corn borers, and other members of the order Lepidoptera.

Unfortunately, the effectiveness and usefulness in the field of many microbial insect pathogens as insecticides are severely limited by their extreme sensitivity to sunlight. It is known, for example, that one of the problems encountered when using *B.t.* as an insecticide is its short period of effectiveness in the field, which is due, in part, to sunlight-induced inactivation of the microorganism. It is also known that nonionizing radiation having a high photon energy (e.g. ultraviolet rays) exerts an inactivating effect on *B.t.* See, "Photoprotection Against Inactivation of *Bacillus thuringiensis* Spores by Ultraviolet Rays," Aloysius Krieg, *Journal of Invertebrate Pathology*, Vol. 25, pp. 267–268 (1975). In particular, it is known that ultraviolet (UV) rays with a wavelength of 253.7 nm induce a marked, extraordinary inactivation of *B.t.* spores, so that they are unable to germinate and grow out. A dosage of 18 m W sec/cm$^2$ of such 253.7 nm wavelength radiation will inactivate 99.9% of the *B.t.* spores. However, since UV radiation of wavelengths shorter than about 285 nm do not reach the earth's surface, such inactivation at 253.7 nm is of little practical concern in the field.

We have determined that the half life of *B.t.* subjected to sunlight is approximately six minutes. Likewise, it has been determined by others that the half lives of certain occluded viruses subjected to sunlight is one-half to one hour. Thus, the effectiveness of a typical spray application of such microbial insecticides is rapidly lost in the field.

Since nucleic acids show a maximum of extinction near a wavelength of 260 nm, it has been suggested by others that the UV induced death of *B.t.* at 253.7 nm, and of certain occluded viruses at comparable wavelengths, may be caused by a photoreaction of the genetic material, especially DNA. Thus, it has been suggested, ibid., at p. 267, that *B.t.* spores could be protected from inactivation by such UV radiation (253.7 nm) by physically mixing the *B.t.* spores with DNA, or a comparable nucleic acid which would absorb the UV rays. Such a comparable nucleic acid would be RNA, Ribonucleic Acid, which has a maximum of extinction near 260 nm. However, this technique proved to be ineffective. Furthermore, as noted above, since wavelengths shorter than about 285 nm do not reach the earth's surface, the usefulness of DNA or RNA as a protectant against sunlight-induced (i.e. at wavelengths greater than about 285 nm) inactivation is unproven.

SUMMARY OF THE INVENTION

The present invention comprises a microbial insecticide composition and methods for the production and utilization of such composition. Typically the composition comprises a microbial insect pathogen of viral, bacterial, or fungal origin which is susceptible to sunlight-induced inactivation embedded in a coacervate microbead which is comprised of a nucleic acid, typically RNA, and a proteinaceous material, whereby the microbead structure itself effectively shields the pathogen from sunlight-induced inactivation. The microbead is typically stabilized by chemical crosslinking.

One typical method for preparing the microbial insecticide composition comprises: (a) preparing a paste-like mixture comprising (i) nucleic acid particles, (ii) proteinaceous material particles, (iii) microbial insect pathogens of viral, bacterial, or fungal origin, and (iv) an amount of water sufficient to wet (i.e. hydrate) substantially the entire mixture; and (b) agitating the paste-like mixture in a manner adapted to break up the mixture into discrete microbeads, whereby the microbial insect pathogens are embedded in the microbeads. Preferably the discrete microbeads are stabilized by treatment with a chemical crosslinking agent such as tannic acid, glutaraldehyde or a similar agent. In one preferred embodiment of the invention the agitation of the paste-like mixture takes place in a solution containing the chemical crosslinking agent.

Another typical method for preparing the composition comprises: (a) preparing an aqueous solution containing a nucleic acid; (b) preparing an aqueous solution containing a proteinaceous material; (c) preparing an aqueous suspension of strongly positively or negatively surface-charged microbial insect pathogens; and (d) mixing the aqueous solutions and suspension prepared in steps (a), (b), and (c) together, thereby spontaneously forming microbeads having the insect pathogens embedded therein. In one preferred embodiment the suspension prepared in step (c) is first mixed with the solution prepared in step (a), and then this mixture is mixed with the solution prepared in step (b). In another preferred embodiment the suspension prepared in step (c) is first mixed with the solution prepared in step (b), and then this mixture is mixed with the solution prepared in step (a).

Typically the surface change of the pathogens is made strongly negative or strongly positive by the addition of a protein-modifying agent to a buffered aqueous suspension of the pathogens. The microbeads are typically crosslinked.

The present invention also comprises a method for controlling insect pests in insect infested areas which typically comprises applying an effective amount of the insecticide composition described above to the insect infested areas.

The present invention further comprises the insecticide composition made by the processes described above.

BRIEF DESCRIPTION OF THE DRAWINGS

In FIGS. 2-4 the number of viable spores, extrapolated to 1 ml of original sample, is shown as a function of the length of time of exposure to the UV radiation. In FIGS. 5, 6, and 8 the percentage of microbes remaining as survivors is shown as a function of the exposure time. In FIGS. 7 and 10 the number of viable spores per filter is shown as a function of the exposure time. FIGS. 9, 11, and 12 show $LD_{50}$ data as a function of the exposure time.

DETAILED DESCRIPTION OF THE INVENTION

In the present invention, microbial insect pathogens of viral, bacterial or fungal origin which are susceptible to sunlight-induced inactivation are embedded in coacervate microbeads comprised of a nucleic acid, typically RNA, and a proteinaceous material. We have found that such microbeads provide excellent protection of the pathogens against sunlight-induced inactivation. The microbeads act as protective shields, serving to intercept and block the harmful radiation wavelengths (i.e. those wavelengths of sunlight which tend to inactivate the pathogen) before they reach the light-sensitive material of the insect pathogen.

We have successfully embedded Douglas fir tussock moth nuclear polyhedrosis virus, *Autographa californica* nuclear polyhedrosis virus, *Bacillus thuringiensis* cells, spores, and toxin crystals, and the following vegatative bacterial cells: *Pseudomonas fluorescens, Serratia marcescens,* and *Escherichia coli* in the microbeads of the present invention. Based on this, we believe that any microbial insect pathogen, whether of viral, bacterial, or fungal origin, including, but not limited to, the insect pathogens disclosed in *Microbial Control of Insects and Mites,* H. D. Burges and N. W. Hussey, Eds., Academic Press, 1971, may be successfully embedded in the microbeads of the present invention. Furthermore, based on the experimental data reported in the Examples below, there is little doubt that any insect pathogen embedded in such microbeads will be protected against sunlight-induced inactivation.

Various proteinaceous materials may be used in combination with the nucleic acid to form the microbeads, depending on the specific insect pathogen to be protected and the microbead system to be used, including, but not limited to: protamine, cytochrome c, soy protein, hemoglobin, gelatin, synthetic amino acid polymers, etc. In general any proteinaceous material can be used if the conditions are adjusted so as to facilitate formation of the microbeads. Such conditions may include charge modification techniques, adjustments in pH, component concentrations, etc.

The microbeads in which the microbial insect pathogens are embedded may be advantageously produced using known techniques for forming what have been called coacervate droplets or microbeads. One such technique was developed in conjunction with the study of the origin of life on earth, and has been used to construct precellular models. See, for example, Evreinova, et al., *Journal of Colloid and Interface Science,* Vol. 36, No. 1 (1971). According to this technique, an aqueous solution containing a nucleic acid (preferably ribonucleic acid, RNA) and, if necessary, a buffering agent (e.g. sodium phosphate or sodium acetate) designed to maintain the pH at a position which optimizes the charge on the nucleic acid, the protein and the microbe, e.g. with respect to the desired pI (where the microbe is sensitive to pH, this should be taken into account as well), is mixed with an aqueous solution containing an appropriate proteinaceous material. Proteinnucleic acid microbeads which are essentially solid and roughly spherical form spontaneously upon the mixing of these two solutions. In the discussion which follows, the above-described technique will be referred to as the "solution formulation" technique, and microbeads formed according to this technique will be referred to as "solution formulation" microbeads.

In an equally preferred embodiment of the invention the microbeads in which the microbial insect pathogens are embedded may be produced using a new technique which we have developed. In the discussion which follows, this new technique will be referred to as the "paste formulation" technique, and microbeads formed according to this technique will be referred to as "paste formulation" microbeads. According to this new paste formulation technique, a paste-like mixture is prepared comprising nucleic acid (preferably RNA) particles, proteinaceous material particles, and an amount of water sufficient to wet substantially the entire mixture, and then this paste-like mixture is agitated in a manner designed to break up the mixture into discrete microbeads. Such agitation may be accomplished by conventional techniques such as, for example, rapid stirring or blending (in a conventional blender), sonification, shaking, pressure extrusion, etc. In order to facilitate the breaking up of the mixture into discrete microbeads, it may be desirable, in certain embodiments, to extrude the paste-like mixture into filaments, pellets, etc. prior to agitation. It is generally preferred to stabilize the discrete microbeads by treatment with a chemical cross-linking agent (e.g. tannic acid, etc.) either during or after agitation. However, crosslinking may be unnecessary where stabilization may be effected by other means, such as, for example, freeze drying.

With respect to the solution formulation technique, and to a certain extent the paste formulation technique, it should be noted that while all of the above-named proteinaceous materials, and others, can be used satisfactorily in forming the microbeads, care must be taken to maintain the pH of the mixture of solutions on the acid side of the isoelectric point of the particular protein being used, since this is required for formation of the microbeads. For example, when using protamine the pH should be maintained below about 11, and when using hemoglobin the pH should be maintained below about 7. Furthermore, if a protein is used that is insoluble at a given pH, the pH may have to be put in a range in which the protein is soluble, or other steps may have to be taken to make the protein soluble. These steps could include partial degradation, charge modification or adding other components in the buffers (e.g. detergents, alcohols, surfactants, etc.). If foaming of one or more components is a problem, simethicone type agents (U.S. Pat. No. 2,441,098) can be included. When RNA is being used as the nucleic acid in the solution formulation technique, the pH of the mixture of solutions must be maintained at or above about 4.3 to prevent the RNA from precipitating out of the microbead, with the protein necessarily leaving the microbead and going back into solution.

As can be seen, in the above-described solution and paste formulation techniques for forming microbeads (i.e., coacervate droplets), the materials to be utilized to intercept and absorb the harmful radiation form the microbead structure, thereby producing a highly protective coating.

The bimolecular structure of the microbeads creates a thermodynamically stable cooperation between the components, so that even without subsequent chemical crosslinking, as described below, the components will not individually diffuse out of the microbeads. The bimolecular structure also causes the microbeads to be highly charged. These charges should aid the microbeads in sticking to plant surfaces. These charges can be controlled by selecting the appropriate protein to be used in forming the microbead.

It has been reported that, the size of the microbeads (solution formulation) can be controlled by controlling the concentration of the nucleic acid and the protein in the formation vessel. We have determined, for example, that $100\mu$ diameter solution formulation microbeads can be made by mixing an equal volume of 5% RNA and 10% protamine sulfate. Microbeads will form and settle to the bottom of the vessel. Most of these will be in the $100\mu$ range. We have also found that the size of the microbeads can be controlled, to some extent, by the degree of agitation during formation, with greater agitation producing smaller microbeads. While microbeads having an effective diameter within the range of from about 10 to about 200 microns should be suitable for use in the present invention, it will generally be preferred to utilize microbeads having an effective diameter within the range of from about 40 to about 100 microns. In general, the type of vegetation (i.e. crops, trees, etc.) to be treated and the method of application will determine the desired microbead size.

While a relatively wide range of nucleic acid and proteinaceous material concentrations can be used to make these microbeads generally, in preparing microbeads for use in the present invention (i.e. for entrapping microbial insect pathogens) it is preferred to use a nucleic acid: protein ratio in the range from about 1:5 to 5:1.

In those embodiments of the invention wherein it is desired to utilize the solution formulation microbeads described above, the microbial insect pathogens may be embedded (i.e., entrapped) in the microbeads by simply placing them in suspension in water (a buffering agent, e.g. phosphate, acetate, etc. may optionally be added if necessary to control pH) and then mixing this suspension with an aqueous solution containing the desired nucleic acid. The resulting suspension is then mixed with the aqueous protein solution as described above and the pathogen is spontaneously embedded in the proteinaceous material-nucleic acid microbeads which form. As a less preferred alternate procedure, the buffered suspension of microbes may be first mixed with the proteinaceous material solution and then the resulting suspension mixed with an aqueous solution containing the nucleic acid. It has been found that subsequent shaking of the vessel in which the solutions have been mixed will cause the microbeads to coalesce and spontaneously reform, usually resulting in additional pathogens being embedded in the microbeads.

In those embodiments of the invention wherein it is desired to utilize the paste formulation microbeads described above, the microbial insect pathogens may be embedded in the microbeads by simply placing them in suspension in water (as above, a buffering agent may be added as necessary) and then mixing this suspension with the mixture of nucleic acid particles and proteinaceous material particles (care should be taken to use only an amount of water sufficient to wet the mixture and give it a paste-like consistency). The resulting paste-like mixture is then agitated as described above so as to break it up into discrete microbeads. As an alternative procedure, nucleic acid particles and proteinaceous material particles may be mixed with an amount of water sufficient to wet the mixture and give it a paste-like consistency, and then the microbial insect pathogens may be mixed with this paste-like mixture and embedded in discrete microbeads by agitation of the mixture as described above.

While the microbeads produced according to the above-described solution formulation and paste formulation techniques possess a certain degree of stability, it will generally be advantageous to increase their stability to faciliate separation of embedded pathogens from non-embedded pathogens and to further facilitate handling. This is particularly so with respect to paste formulation microbeads. In a preferred embodiment of the invention, such stabilization is accomplished by chemically crosslinking the microbead molecules by treating them with crosslinking agents such as, for example, tannic acid, glutaraldehyde, imidoester agent, dithiobis-succimidyl propionate, etc. using conventional crosslinking techniques. If it is desired to use glutaraldehyde, an aqueous solution of 0.25%, or less, (by weight) should be used, since we have found that as the glutaraldehyde concentration is increased, certain pathogens, in particular, *Bicillus thuringiensis*, will tend to become inactivated. We have found that buffered tannic acid is non-toxic to bacterial spores at a concentration of 10% (w/v), and we believe that it will be non-toxic to most microbial insect pathogens at concentrations of 1% or less (w/v). While buffered tannic acid having a concentration within the range of from about 0.001% to 10% should be suitable for use, concentrations within the range of from about 0.5% to 1.5% will generally be preferred.

It should be noted that the depth of crosslinking can be controlled rather easily by controlling the time, concentration, temperature, and other conditions of crosslinking. For example, the depth of crosslinking may be controlled by stopping the crosslinking reaction by adding a small molecule which reacts with the crosslinking reagent (e.g lysine added to glutaraldehyde) or by using low crosslinking reagent concentrations.

Such chemical crosslinking of the microbeads yields several advantages, including: (1) stabilization against the shear forces created by spray application of the insecticide; (2) maintenance, if desired, of fluid centers within the microbeads; (3) maintenance, if desired, of a pH level inside the microbead which is lower than that of the environment surrounding the microbead (i.e., alkaline digestive juices of the insect gut) so that the interior of the microbead may be kept at a pH value near the optimum pH value for viability, storage, etc. of the microbial pathogen; (4) control of the position in the insect gut where the pathogen is released (i.e. the greater the crosslinking, the further along in the gut release will occur and vice-versa), thereby increasing the infectivity of the pathogen. In addition, the use of tannic acid as the crosslinking agent increases the optical density of the resulting crosslinked microbeads (see FIG. 1), thereby providing improved shielding of the embedded microbes against sunlight-induced inactivation.

We have also found that the microbial insect pathogen may be embedded (i.e. entrapped) in the above-described solution formulation microbeads much more readily and in much greater numbers if its net surface charge is first modified so as to be made nearly totally (i.e. strongly) negative or nearly totally positive. We believe this will also be the case with regard to paste formulation microbeads. This surface charge modification may be accomplished, for example, by the controlled addition of a protein modifying agent such as, for example, succinic anhydride (to make strongly negative) and similar compounds (see e.g., Gary E. Means and Robert E. Feeney, *Chemical Modifications of Proteirs*, Holden Day, Inc., 1971). However, care must be taken to select a protein-modifying agent which will not inactivate or harm the pathogen to be embedded. For example, we have found that succinic anhydride is not suitable for use with vegetative bacterial cells (e.g. *Serratia marsescens*, etc.), since it tends to inactivate these cells. Modification to a strongly positive surface charge may be accomplished, for example, by using tannic acid to link positively charged proteins (e.g. protamine) to the surface of the pathogen. We have found, in comparative studies, that in the absence of any charge modification, only about 1% of the available *B.t.* spores are embedded in the microbeads (solution formulation), and that using strongly negatively surface charged *B.t.* spores (succinic anhydride treatment) results in about 10–20% of the *B.t.* spores being embedded in the microbeads, and that using strongly positively surface charged *B.t.* spores (treatment with tannic acid then protamine sulfate) results in about 20–40% of the *B.t.* spores being embedded in the microbeads. The effectiveness of these charge modification techniques may be increased by first washing the microbial insect pathogen, and it may be desirable, in certain embodiments, to wash in separate organic (e.g. 60% ethanol solution, by weight) and inorganic (e.g. 1 M sodium chloride solution) washes, provided the pathogen being used is not sensitive to such materials. We have found that, prior to attempting any of the above-described charge modification techniques on insect viruses, it will generally be preferred to purify the viruses (e.g. by centrifugation, filtration, etc.) in order to remove the insect debris.

Since the charge-modified pathogen apparently competes with the like-charged component of the microbead for positions in the bead, it may be necessary to reduce the concentration of such like-charged component to a level which will faciliate incorporation of the pathogen into the microbead. For example, if it is desired to entrap microbial insect pathogens which have been modified to a strongly negative surface charge in an RNA-protein microbead as described above, it may be necessary to reduce slightly the concentration of the RNA solution (RNA is also negatively charged) prior to mixing with the protein solution.

Figure 1:
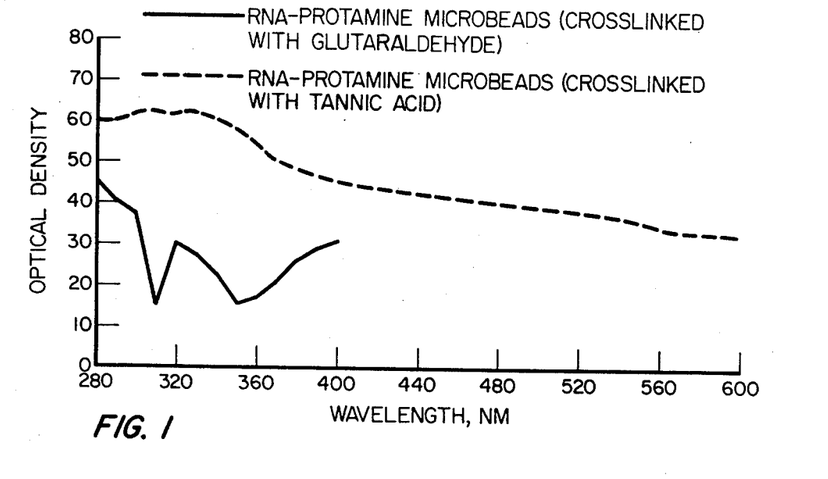
FIG. 1 is a graph showing the optical density, over the solar UV and visible range, of two typical types of microbeads suitable for use in the present invention.

Likewise, in such a microbead system, if the surface charge of the pathogen has been modified to a strongly positive surface charge, then it may be necessary to reduce slightly the concentration of the protein solution (protein is positively charged) prior to mixing with the RNA solution. This latter system may be more attractive for purposes of the present invention since it does not require reduction of the amount of radiation-absorbing material (i.e. RNA). inactivation by harmful radiation from the sun, it is obviously important, in selecting the materials to be used in formulating the microbeads, to select materials which strongly absorb and/or reflect such harmful radiation. Preferred materials for use in constructing the microbeads are RNA (ribonucleic acid) and a proteinaceous material such as, for example, hemoglobin, protamine, or a synthetic amino acid polymer. The optical density (i.e. absorption+reflection) of microbeads comprised of RNA and protamine, produced according to the above-described solution formulation technique, is shown in FIG. 1. The solid line in FIG. 1 shows the optical density of a solution of microbeads made by combining equal volumes of 0.33% RNA and 0.5% Protamine (crosslinked with glutaraldehyde) over the solar UV range. The dashed line in FIG. 1 shows the optical density of a solution of microbeads made by combining equal volumes of 0.67% RNA and 1% Protamine (crosslinked with tannic acid) over the solar UV and visible (to 600 nm) range.

In many cases the presence of a nucleic acid in the microbead will offer a second advantage. It has been suggested that the damage caused by wavelengths of sunlight greater than 313 nm is, in the case of many microbes, primarily the result of the reaction of the microbe's nucleic acids with free radicals (it is believed that radiation damage to tyrosine produces $H_2O_2$ which, in turn, produces free radicals). The nucleic acid present in the microbead structure will tend to react specifically with the free radicals which would otherwise react with the microbe's nucleic acids, thus preventing any damage.

Since the pathogenic effect of the microbial agent cannot be realized so long as the agent remains embedded within the microbead, care must be taken in selecting the materials to be used in formulating the microbeads to select those which will permit release of the agent after ingestion of the microbeads by the insect. While other materials might be selected, we have found that microbeads comprised of a protein and a nucleic acid (e.g. RNA) provide quite satisfactory release characteristics.

After ingestion of the microbeads by the insect, the microbeads will be attacked by proteases and nucleases in the insect digestive tract (i.e., gut), which will lead to release of the microbe. Thus, it is important to select microbead materials which are not resistant to such type of attack. We have found that if *Bacillus thuringiensis* (cells, spores and toxin crystals) embedded in microbeads comprised of RNA and protamine (produced according to the above-described solution formulation technique) are incubated at room temperature in the presence of insect digestive juices, release of the *B.t.* begins within minutes, with progressive and complete release following within one half hour.

We have also found that if *Bacillus thuringiensis* embedded in microbeads comprised of RNA and protamine (produced according to the above-described technique) are incubated at room temperature in the presence of amino acids and/or sugars such as would be found in an insect digestive tract, the germinating spores themselves dissolve the microbeads in approximately two hours. This does not occur in water or buffer alone, so that the microbeads will remain intact on leaf surfaces.

Figure 9:
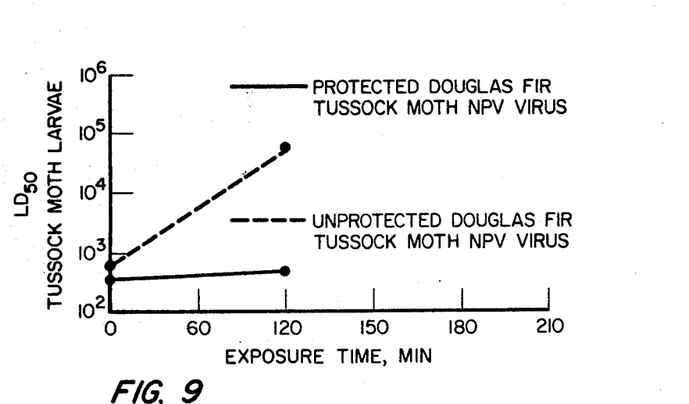
Figure 10:
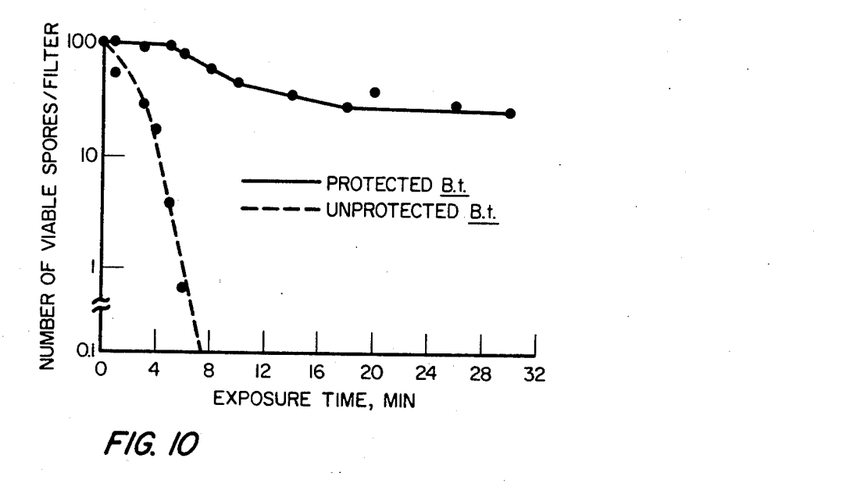
Figure 11:
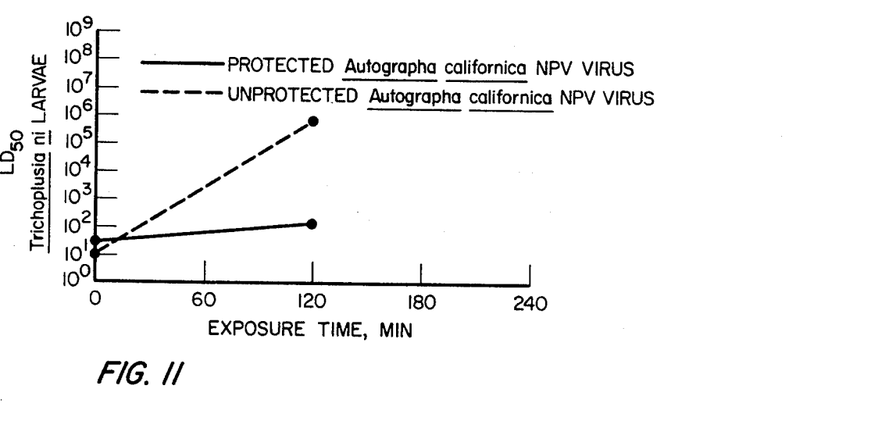
Figure 12:
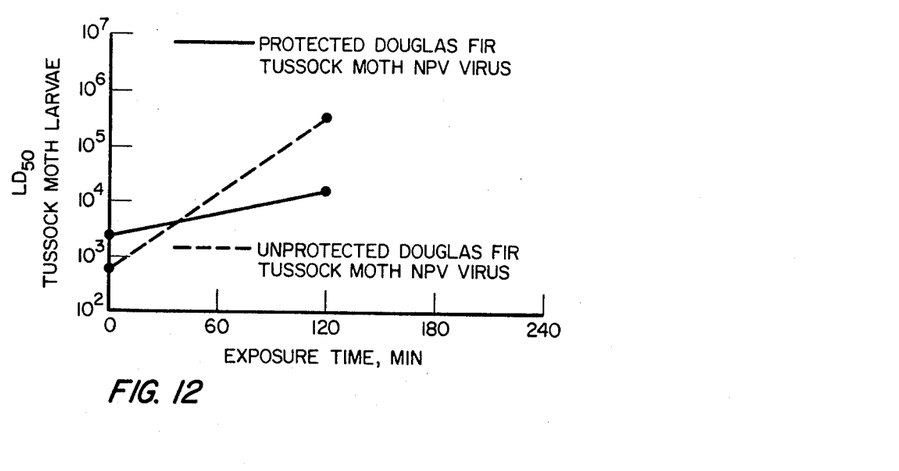

Furthermore, the experimental data shown in FIGS. 9, 11 and 12 indicate the Douglas fir tussock moth NPV viruses and *Autographa californica* NPV viruses embedded in the microbeads of the present invention are, in fact, released in the insect gut, and that upon being so released they exert a killing effect as desired.

It should be noted that the present invention is suitable for use with any light sensitive microbial insect pathogen, including those of viral, bacterial, or fungal origin. Examples 1–5, 7 and 10 below, illustrate the applicability of the present invention to a typical spore-forming bacteria (i.e. *B.t.* cells, spores, and toxin crystals), and Example 8, below, illustrates the applicability of the invention to three species of vegetative bacterial cells. Example 6, below, shows the applicability of the present invention to a bacterial virus. The positive results shown in Example 6 indicate that the present invention should be suitable for use in protecting non-occluded insect viruses against sunlight induced inactivation. Examples 9, 11 and 12 illustrate the applicability of the present invention to two species of occluded insect viruses.

In the Examples (and FIGS. ) which follow, the microbial insect pathogens which are labelled and/or referred to as "unprotected" comprise pathogens which were not embedded in microbeads. In each example the "unprotected" pathogens were treated, exposed, and tested for viability in a manner as nearly identical as possible to the pathogens which were embedded in microbeads (i.e. the "unprotected" pathogens constituted control experiments).

The following Examples illustrate several different embodiments of the present invention. It is intended that all matter in these Examples and in the foregoing description of the preferred embodiments and accompanying drawings be interpreted as merely illustrative and not in a limiting sense.

EXAMPLE 1

$1 \times 10^9$ spores of *Bacillus thuringiensis*, including bacterial cells, spores and asporal (crystalline) bodies, obtained from a sporulation medium culture, were mixed in 10 ml of a 0.15 N phosphate buffer at pH 7.5. 1.5 ml of this solution was mixed with 1.5 ml of a buffered 1.34% aqueous solution (by weight) of yeast RNA (obtained from Sigma as grade B). Then 0.4 ml of this suspension was mixed with constant stirring in 1.9 ml of a buffered 0.36% aqueous solution (by weight) of protamine sulfate (obtained from Sigma as grade B).

RNA-protamine microbeads formed spontaneously, each entrapping some of the bacterial cells and/or spores and/or asporal bodies. Shaking the mixture resulted in breakage and subsequent spontaneous reformation of additional microbeads. The microbeads were placed in a glass petri dish and exposed to a General Electric G30T8 30 watt germicidal lamp. The petri dishes were placed on a rotary shaker 78 cm below the lamp and shaken at 40 rpm. Viability was determined by plating on brain heart infusion agar obtained from Difco.

Figure 2:
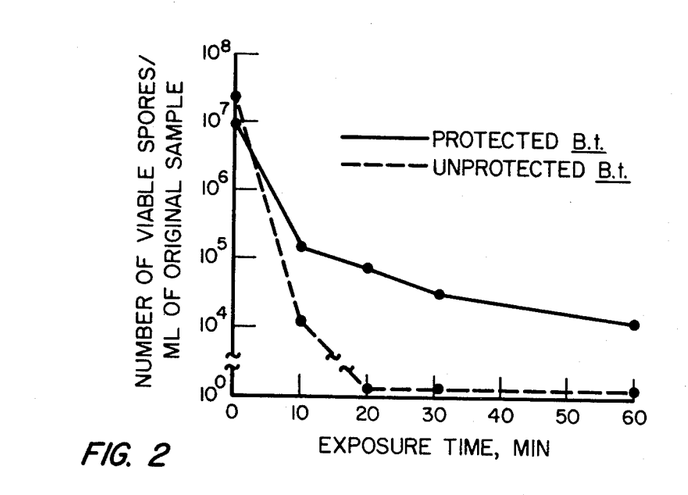
FIGS. 2-12 are graphs showing the comparative experimental data from Examples 1, 2, and 4-12, below, respectively.

When exposed to germicidal ultraviolet radiation (peak radiation at 254 nm) sufficient to kill 99.99% of any unprotected *B.t.* the *B.t.* which was embedded in the microbeads (i.e., the protected bacterial cells and/or spores and/or asporal bodies) nearly all survived. This is shown in FIG. 2. The early die-off shown by the line marked "protected *B.t.*" is thought to be due to the low percentage of *B.t.* actually embedded in the microbeads. Under microscopic observation the percentage of *B.t.* actually embedded was observed to range from 0.5% to 1.5%.

EXAMPLE 2

Figure 3:
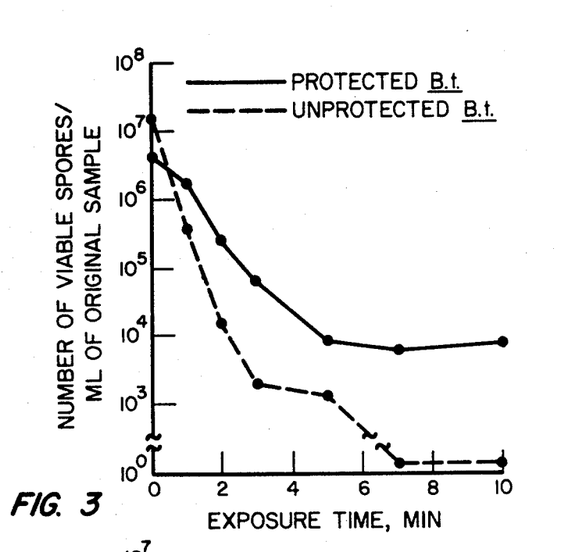

Microbeads with *B.t.* embedded therein were prepared as in Example 1, and then 1 mg/ml dithiobissuccimidyl propionate in DMSO was added to crosslink and stabilize the microbeads. 0.2 ml of this solution were placed on a 0.22$\mu$ Millipore filter and allowed to dry under vacuum. The filters were exposed as in Example 1 without shaking. After shaking, the filters were washed off in dilution buffer and plated as in Example 1. Results of this procedure are shown in FIG. 3.

EXAMPLE 3

$1 \times 10^9$ spores of *B.t.* obtained from culture in sporulation medium were first washed in a 60% ethanol solution and then washed in a 1 M NaCl solution, with the *B.t.* being separated from these washes by centrifugation. The washed *B.t.* was then suspended in 20 ml of a 1 M carbonate buffer solution at a pH of 8.0.

Next, dry succinic anhydride, a protein modifying agent, was added to the suspension as six separate additions of 2.5 mg/ml each. The additions were made under constant stirring and the mixture was stirred for 10 minutes between each addition. The pH was held at $8.0 \pm 0.1$ by addition of NaOH. When the reaction was completed, as indicated by the pH ceasing to change, the *B.t.* was separated out (centifuged) and washed.

This modified *B.t.* (negatively charged) was then incorporated into RNA-protamine microbeads according to the procedures set forth in Example 1 and the microbeads were crosslinked as in Example 2.

It was found that this modified *B.t.* entered the microbeads much more readily and in much higher numbers than the unmodified *B.t.* used in Examples 1 and 2. Presumably this was due to the modification of the surface charge on the *B.t.* from neutral to negative.

EXAMPLE 4

A solution of unprotected *B.t.* (cells, spores, and toxin crystals) and protected *B.t.* (i.e., embedded in microbeads as described in Example 3, but without crosslinking), 60% unprotected and 40% protected (determined microscopically), was subjected to 254 nm radiation as described in Example 1.

Figure 4:
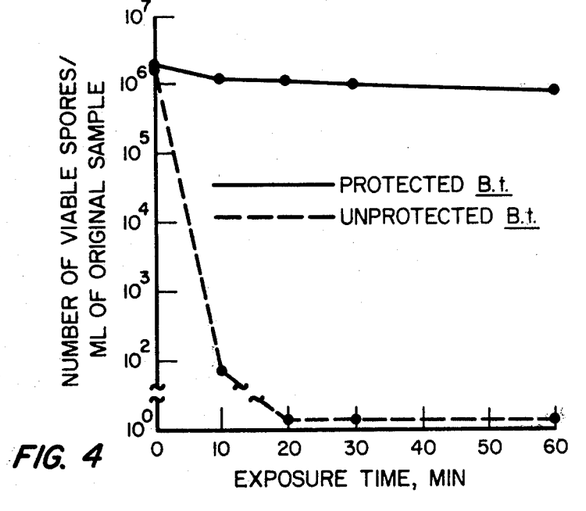

Essentially no unprotected spores remained viable after 15 minutes of such irradiation, while $1 \times 10^6$ protected spores (i.e., 40% of the total original mixture) remained viable after one hour of such irradiation. Viability was determined as in Example 1. The results of this experiment are shown in FIG. 4.

EXAMPLE 5

A concentration of $1 \times 10^9$ spores of *Bacillus thuringiensis* (including cells, spores and asporal crystals) of *B.t.* was suspended in 10 ml of 0.15 N phosphate buffer, pH 7.5 (*B.t.* preparation was obtained and modified as in Example 3). 0.5 grams of RNA (Calbiochem, grade B)

was dissolved into this suspension and mixed by vigorous mixing in a Vortex mixing device. The suspension was then added to a buffered 10% solution of protamine sulfate (Calbiochem, grade B, by weight) and vigorously shaken for 5 seconds. Glutaraldehyde (25%, from Sigma) was added to the solution to a final concentration of 0.15% (by volume). After 30 minutes a pellet formed at the bottom of the tube which consisted of large microbeads (100–150μ). The supernate was drawn off and the pellet was resuspended to a final volume of 20 ml by shaking. This solution was placed on a 0.22μ Millipore filter and dried overnight under vacuum. The filters were exposed to sunlight (1:00 pm, RH 23%, temperature 89° F.). The filters were then washed in acetate buffer (0.15 N, pH 4.0) to break up the microbeads and release the *B.t.*, which was plated as in Example 1.

Figure 5:
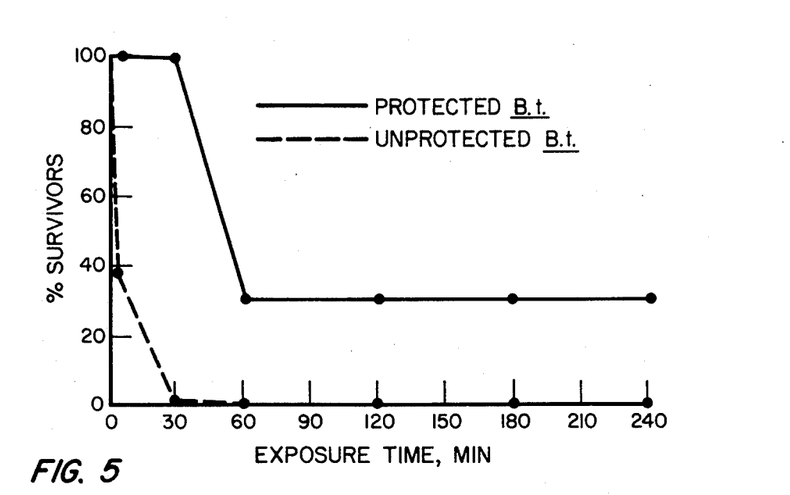
Figure 6:
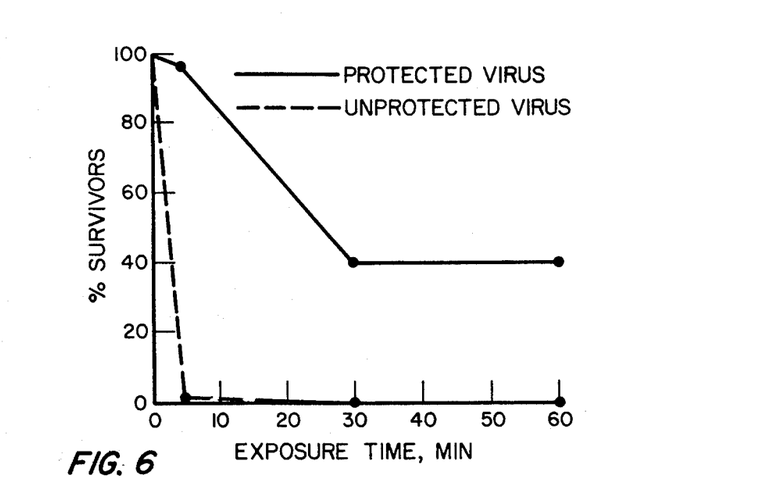
Figure 7:
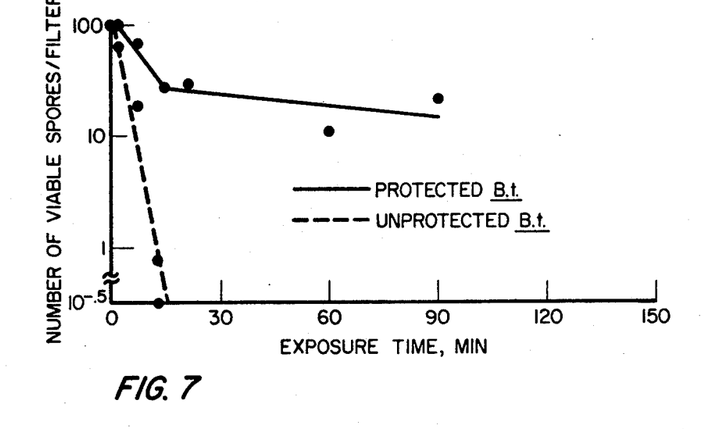
Figure 8:
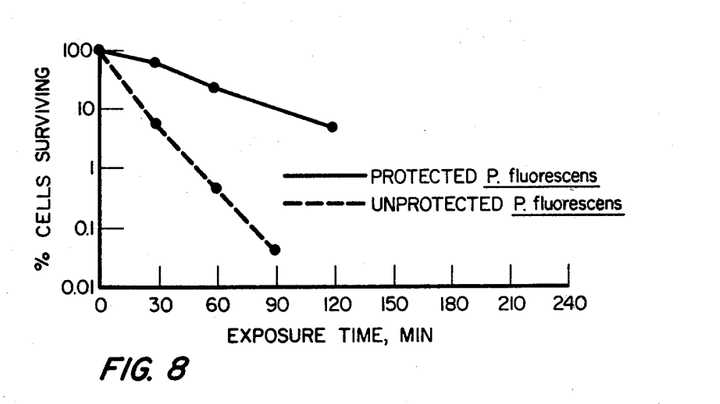

The results of this experiment are shown in FIG. 5. Unprotected spores were nearly all killed after 30 minutes.

EXAMPLE 6

The purpose of this example was to demonstrate protection of a virus according to the present invention. The reactions and response of an insect virus and a bacterial virus (called bacterial phage) should be similar since both are composed basically of a nucleic acid in a protein coat. Accordingly, we chose to model our system with the bacterial virus of *E. coli*, phage T-4.

T-4 bacterial phages were grown in nutrient broth with 0.5% NaCl (P-broth). *E. coli* BB was inoculated into 100 ml P-broth and allowed to grow overnight. In the morning a 1:100 dilution was made to fresh broth and growth was allowed to proceed for one hour. $1\times10^7$ phages were added to this rapidly growing *E. coli* BB culture and allowed to grow for six hours (37° C., rapid shaking). At the end of the period, 5 drops of chloroform were added to kill all bacteria in the culture. This is the phage stock.

Microbeads were prepared by mixing 0.100 grams of protamine sulfate (Calbiochem, grade B) in 10 ml phage stock. This suspension was added to 1% RNA (by weight) in P-broth. The microbeads formed spontaneously. The UV exposure was carried out as in Example 1. Timed samples were taken and dilutions were made in P-broth. The viable phages were determined by the method described in the following text: Grace C. Rovozzo and Carroll N. Burk, *A Manual of Basic Virological Techniques*, Prentice-Hall Biological Techniques Series, 1973, page 168, using P-broth agar and *E. coli* BB as the indicator bacteria.

The results of this experiment are shown in FIG. 6. These data show that unprotected virus were all killed in approximately 5 minutes. On the other hand, after an initial drop similar to that seen in the bacterial tests, the virus which was embedded in the microbeads show strong UV light resistance (approximately 40% are protected from inactivation).

EXAMPLE 7

Microbeads having *B.t.* (cells, spores, and toxin crystals) embedded therein were prepared as in Example 3, except that dithiobissuccimidyl propionate in DMSO was not used to crosslink the microbeads. In this example the microbeads were crosslinked and stabilized by adding phosphate-buffered tannic acid (1% w/v) to the microbead suspension, and allowing it to stand at room temperature for about 30 minutes. The suspension of crosslinked microbeads was diluted with dilution buffer (phosphate) in a manner selected to produce a diluted suspension containing approximately 100 spores per ml, and 1 ml samples of this diluted suspension were pulled onto separate 0.22μ Millipore ® filters and permitted to dry overnight. The filters were exposed under a General Electric sunlamp measured at 1572 watts/$m^2$ at 15 inches and providing radiation in the wavelength range of about 290 nm to 400 nm. One hour exposure under this sunlamp was equivalent to approximately 151 hours under direct sunlight on a July day at a location of approximately 45° latitude (i.e. about 15 days). After exposure, the spores were placed directly on plate count agar, and after 24 hours incubation the colonies growing on the filters were counted. The experimental data are shown in FIG. 7.

EXAMPLE 8

Vegetative bacterial cells of the species *Pseudomonas fluorescens*, *Serratia marcescens*, and *Escherichia coli* were treated with succinic anhydride, in three separate series of experiments, by placing approximately $1\times10^9$ cells in 20 ml of 1 M carbonate buffer solution (at pH 8.0), then adding 50 mg of succinic anhydride. The pH was not maintained because the resultant pH, about 7.5, was believed to be more advantageous for bacterial survival during harvesting and washing. The succinic anhydride treated cells of the three species were suspended, again in separate tests, in 4 ml of a 0.15 N phosphste buffer solution (at pH 7.5), and 1 ml of this suspension was then mixed with 1 ml of a buffered 1.34% (w/v) RNA (obtained from Sigma) solution. The resulting suspension was mixed with 2 ml of a buffered 1% (w/v) Protamine sulfate (obtained from Cal Biochem.) solution, spontaneously forming the microbeads, and then 0.4 ml of a 10% (w/v) tannic acid solution was added to the suspension of microbeads. (Note: the buffer referred to above was 0.15 N phosphate buffer solution at pH 7.5). The suspension of microbeads in tannic acid was allowed to stand for 30 minutes at room temperature, and then was washed three times in the phosphate buffer solution described above by centrifuging.

Microscopic observation revealed that approximately 30% of each of the three species tested were embedded in the microbeads.

The suspensions of microbeads produced in the three series of experiments were exposed, separately, under the General Electric sunlamp described in Example 7 using the experimental procedure described in Example 1 (i.e. exposure while on a rotary shaker), except that a greater number of microbeads were present in the suspension. Data from a representative test of the *P. fluorescens* bacterial cells are shown in FIG. 8. The data from the tests of the *Serratia marcescens* and *Escherichia coli* bacterial cells (not shown) were similar to that shown in FIG. 8.

It should be noted however, that in performing the experiments for which data are shown in FIG. 8, it was assumed that any bacterial cells in the microbead suspension which had not been embedded in the microbeads would be killed during exposure of the suspension while on the rotary shaker. To test the correctness of this assumption a second control experiment (in addition to the control shown in FIG. 8) was run. In this second control, *B.t.* spores were treated as described above, except that they were not embedded in microbeads, but were merely mixed in a suspension containing already-formed microbeads (using approximately the same number of microbeads as used in the experiments described above), and this mixture was exposed under the sunlamp as described above. If the assumption was correct, then most of the cells should be killed. We found, however, that the cells were killed at roughly the same rate as the cells which had been embedded in the microbeads. We attribute this to the relatively large number of microbeads present in the suspensions which were exposed (i.e. the microbead suspensions were too heavy). We believe that the large number of microbeads present restricted the movement of the cells which were outside the microbeads, so that any cells which were underneath a microbead essentially remained there throughout the exposure and were protected. Thus, we feel that this example, including the second control, does show that the microbeads protect the cells against sunlight-induced inactivation (whether the cells are in or outside, but under, the microbeads). Also, as noted above, microscopic observation revealed that cells of each of the three bacterial species tested were embedded in the microbeads.

EXAMPLE 9

$1\times10^8$ Douglas fir tussock moth nuclear polyhedrosis virus was suspended in a 0.5 N phosphate buffer (20 ml) at pH 7.5 and treated with six 50 mg additions of succinic anhydride. 1.0 N NaOH was used to hold thepH at 7.5. After treatment, the virus suspension was harvested by centrifugation and washed twice in 0.15 N phosphate buffer and resuspended in 1 ml of the buffer. This suspension was then treated as described in Example 8 to form crosslinked microbeads having the virus embedded therein. The suspension was exposed under the General Electric sunlamp as described in Example 8, then diluted with buffer and tested for infectivity as described in Example 12. The infectivity data is shown in FIG. 9. This data suffers the same error as described in Example 8 (i.e. microbead suspension which was exposed was too heavy to permit kill off of virus which were not embedded in the microbeads). However, as in Example 8, microscopic observation did reveal that about 30% of the virus was embedded in the microbeads, and that the microbeads offered protection against sunlight-induced inactivation (whether the virus are inside or outside, but under, the microbeads).

EXAMPLE 10

1 gram of hemoglobin (crude powder) was mixed with 0.34 gram of RNA in dry powder form. Approximately $1\times10^9$ spores of *B.t.* were suspended in a buffer solution (0.15 N acetate, pH 5.0), and then added to the RNA-hemoglobin mixture. Additional buffer solution was added in an amount sufficient to form a hydrated (i.e. wet) mass having a paste-like consistency. The total amount of buffer solution mixed with the RNA-hemoglobin mixture was about 1 ml. This paste was forced (i.e. extruded) through an 18 gauge needle (using a 5 cc syringe) into a buffered (0.15 N acetate) 1% (w/v) tannic acid solution and subjected to magnetic stirring in a beaker. After about 30 minutes of stirring, the extruded paste had been broken into discrete, crosslinked microbeads approximately 100$\mu$ or smaller in size having the *B.t.* incorporated therein. The microbead suspension was diluted and exposed under a General Electric sunlamp as described in Example 7 (i.e. on filters). The experimental data are shown in FIG. 10.

EXAMPLE 11

*Autographa californica* nuclear polyhedrosis virus (approximately $1\times10^7$ polyhedral inclusion bodies) was embedded in RNA-Protamine microbeads using the technique described in Example 10. In this example, 1 gram of protamine (dry powder form) and 0.67 grams of RNA (dry powder form) were used, the buffer was 0.15 N phosphate solution at pH 7.5, and tannic acid was used to crosslink and stabilize the microbeads. The microbead suspensions were washed twice in distilled water and then diluted 1:100 in distilled water. The diluted suspensions were exposed under a General Electric sunlamp using the technique described in Example 1, and the exposed suspensions were diluted in phosphate buffer as needed for the infectivity tests, described below. *Trichoplusia ni* larvae were used to measure infectivity of the protected virus (i.e. embedded in the microbeads) and the unprotected virus (i.e. the control). Infectivity was determined by placing 10 $\mu$l of separate dilutions ($1:10^2$ to $1:10^7$) on a 0.2 gram piece of diet. The larvae were allowed to eat the entire piece of diet, and then a new piece of diet (2 grams) was placed in the vial. When all the control larvae (not fed virus microbeads) had pupated, the dead larvae were autopsied to verify that death was caused by infection caused by the *Autographa californica* virus (this was found to be the case). $LD_{50}$'s for the *T. ni.* larvae were determined for virus which had been protected by the microbeads and for the control virus, which had not been protected by an microbeads. The general procedures for making $LD_{50}$ determinations are described in *Microbiology,* at p. 639, B. D. Davis, et al., Harper and Row, 1973. The $LD_{50}$ data are shown in FIG. 11.

EXAMPLE 12

Example 11 was repeated using Douglas fir tussock moth nuclear polyhedrosis visus in place of the Autographa californica virus and Douglas fir tussock moth larvae in place of the *T. ni.* larvae, except that the larvae were autopsied at the end of a 10 day period. The $LD_{50}$ data are shown in FIG. 12.

It should be understood that the term "nucleic acid" as used through this specification and in the claims is intended to include all polynucleotides. Likewise, the term "protein" is intended to include all polypeptides.

It is also to be understood that although the present invention has been specifically disclosed by preferred embodiments and optional features, modification and variation of the concepts herein disclosed may be resorted to by those skilled in the art, and such modifications and variations are considered to be within the scope of this invention as defined by the appended claims.

We claim:

1. A method of making a microbial insecticide composition, comprising (a) preparing a mixture comprising (i) nucleic acid particles, (ii) proteinaceous material particles, (iii) microbial insect pathogens of viral, bacterial, or fungal origin, and (iv) an amount of water sufficient to wet substantially the entire mixture and give it a paste-like consistency; and (b) agitating the paste-like mixture in a manner adapted to break up the mixture into discrete microbeads, whereby the microbial insect pathogens are embedded in the microbeads.

2. A method as in claim 1, wherein the discrete microbeads are stabilized by treatment with a chemical crosslinking agent.

3. A method as in claim 2, wherein the crosslinking agent comprises tannic acid or glutaraldehyde.

4. A method as in claim 2, wherein the agitation of the paste-like mixture takes place in a solution containing the chemical crosslinking agent.

5. A method as in claim 1, wherein the paste-like mixture is prepared by mixing the nucleic acid particles and the proteinaceous particles, separately mixing the microbial insect pathogens and the water, and then mixing these two mixtures together.

6. A method as in claim 1, wherein the paste-like mixture is prepared by first mixing the nucleic acid particles, the proteinaceous particles, and the water, and then mixing the microbial insect pathogens into this mixture.

7. A method as in claims 1 or 9, wherein the nucleic acid comprises ribonucleic acid and the proteinaceous material comprises protamine, hemoglobin, or a synthetic amino acid polymer.

8. A method as in claim 1, wherein the discrete microbeads are subsequently freeze dried.

9. A method of making a microbial insecticide composition, comprising:

(a) preparing an aqueous solution containing a nucleic acid;

(b) preparing an aqueous solution containing a proteinaceous material;

(c) preparing an aqueous suspension of strongly positively or negatively surface-charged microbial insect pathogens; and (d) mixing the aqueous solutions and suspension prepared in steps (a), (b), and (c) together, thereby spontaneously forming microbeads having the insect pathogens embedded therein.

10. A method as in claim 9, wherein the suspension prepared in step (c) is first mixed with the solution prepared in step (a), and then this mixture is mixed with the solution prepared in step (b).

11. A method as in claim 9, wherein the suspension prepared in step (c) is first mixed with the solution prepared in step (b), and then this mixture is mixed with the solution prepared in step (a).

12. A method as in claim 9, wherein the microbeads are stabilized by treatment with a chemical crosslinking agent.

13. A method as in claims 1 or 9, wherein prior to being embedded in the microbeads, the surface charge of the pathogens is made strongly negative or strongly positive by the addition of a protein-modifying agent to an aqueous suspension of the pathogens.

14. A method as in claim 9, wherein prior to treatment with the protein-modifying agent, the pathogens are cleaned by washing.

15. The insecticide composition made by the process of claims 1 or 8.

* * * * *

UNITED STATES PATENT AND TRADEMARK OFFICE
CERTIFICATE OF CORRECTION

PATENT NO. : 4,265,880
DATED : May 5, 1981
INVENTOR(S) : Kemet D. Spence et al.

It is certified that error appears in the above—identified patent and that said Letters Patent is hereby corrected as shown below:

Column 16, line 30: change "8" to --9--.

Signed and Sealed this

Fourteenth Day of July 1981

[SEAL]

Attest:

Attesting Officer

GERALD J. MOSSINGHOFF

Commissioner of Patents and Trademarks